United States Patent [19]

Krespan et al.

[11] 4,363,898

[45] Dec. 14, 1982

[54] PERFLUORODIGLYCIDYL ETHERS

[75] Inventors: Carl G. Krespan; Thomas R. Darling, both of Wilmington, Del.

[73] Assignee: E. I. Du Pont de Nemours and Company, Wilmington, Del.

[21] Appl. No.: 250,907

[22] Filed: Apr. 3, 1981

[51] Int. Cl.$^3$ ............................................. C08G 65/22
[52] U.S. Cl. ..................................... 525/404; 525/407; 526/273; 528/102; 528/361; 528/391; 528/402
[58] Field of Search ............... 528/102, 361, 391, 402; 526/273; 525/404, 407

[56] References Cited

U.S. PATENT DOCUMENTS

| | | | |
|---|---|---|---|
| 2,500,388 | 3/1950 | Simons | 260/614 |
| 2,713,593 | 7/1955 | Brice et al. | 260/535 |
| 3,250,808 | 5/1966 | Moore et al. | 260/535 |
| 3,321,532 | 5/1967 | Lorenz | 260/614 |
| 3,322,826 | 5/1967 | Moore | 260/544 |
| 3,358,003 | 12/1967 | Eleuterio et al. | 260/348 |
| 3,419,610 | 12/1968 | Temple | 260/544 |
| 3,660,315 | 5/1972 | Hill et al. | 260/2 A |
| 4,085,137 | 4/1978 | Mitsch et al. | 260/561 HL |
| 4,127,615 | 11/1978 | Zahir et al. | 260/837 R |
| 4,255,299 | 3/1981 | Daimon et al. | 260/17 R |
| 4,267,302 | 5/1981 | Ohmori et al. | 528/103 |
| 4,275,225 | 6/1981 | Krespan | 560/174 |

OTHER PUBLICATIONS

Ito et al., "Synthesis and Co-Telomerization of 4--Bromo- and 4-Chloroheptafluoro-1,2-Epoxybutanes" Division of Fluorine Chemistry, Abstracts ACS/JCS Chemical Congress, Honolulu, Hawaii, Apr. 1979.

Khrlakyan et al., "Fluorinated Mono- and Diepoxy Compounds", Bull. Acad. Sciences USSR(1), 62-64 (1965), Chemical Series (English Translation).

Tarrant et al., *Fluorine Chemistry Reviews*, vol. 5, Marcel Dekker, New York, 1971, pp. 77-113.

*Primary Examiner*—Earl A. Nielsen

[57] ABSTRACT

Perfluoroglycidyl ethers of the formula

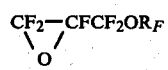

are prepared by epoxidation of a perfluorodiallyl ether of the formula:

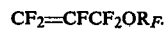

The glycidyl ethers are useful as monomers for preparing polymers which provide crosslinking or cure sites and are stable elastomeric materials useful as sealants, caulks, and fabricated objects.

9 Claims, No Drawings

PERFLUORODIGLYCIDYL ETHERS

TECHNICAL FIELD

This invention relates to perfluorodiglycidyl ethers, their preparation and polymers therefrom.

BACKGROUND ART

P. Tarrant, C. G. Allison, K. P. Barthold and E. C. Stump, Jr., "Fluorine Chemistry Reviews", Vol. 5, P. Tarrant, Ed., Dekker, New York, New York (1971) p 77 disclose fluorinated epoxides of the general formula:

$$CF_2\text{—}CFR_F$$
$$\diagdown O \diagup$$

wherein $R_F$ may be a perfluoroalkyl group of up to 10 carbons containing one or more functional substituents:

$$-CF=CF_2, -CF\diagdown_O\diagup CF_2, -Cl \text{ or } -H$$

Oxidations of the type $$CF_2=CFCF_2X + O_2 \text{ or}$$

$$H_2O_2/OH^- \longrightarrow CF_2\text{—}CFCF_2X$$
$$\diagdown O \diagup$$

are disclosed where X is —F, —(CF$_2$)$_5$H (U.S. Pat. No. 3,358,003), —CF$_2$Cl or —CF$_2$Br (T. I. Ito et al, Abstracts, Div. Fluoro. Chem., Am. Chem. Soc., 1st ACS/CJS Chem. Congress, Honolulu, HI, April 1979)

Oligomers and polymers of perfluoroepoxides $$CF_2\text{—}CF\text{—}R_F$$
$$\diagdown O \diagup$$

are described in U.S. Pat. No. 3,419,610 and by P. Tarrant et al. in Fluorine Chem. Reviews, 5, pp 96–102 (1971). Nonfunctional fluoroethers of difluoroacetyl fluoride of the formula $R_FOCF_2COF$ are also known, and the insertion of one or more moles of hexafluoropropene epoxide into said nonfunctional perfluoroethers is disclosed in U.S. Pat. No. 3,250,808:

$$R_FOCF_2COF + n\ (CF_2\text{—}CFCF_3) \longrightarrow \qquad (1)$$
$$\diagdown O \diagup$$

$$R_FOCF_2CF_2O\text{—}\left[\text{—}CF\text{—}CF_2O\text{—}\right]_{n-1}\text{—}CFCOF$$
$$\qquad\qquad\qquad\ \ |\qquad\qquad\qquad\quad\ |$$
$$\qquad\qquad\qquad\ CF_3\qquad\qquad\qquad CF_3$$

where n is 1 to at least 6 and $R_F$ is perfluoroalkyl, perfluoroalkoxy, or perfluoroalkoxyalkyl.

Glycidyl ethers containing the segment $$CH_2\text{—}CHCH_2O\text{—}$$
$$\diagdown O \diagup$$

are widely disclosed. The glycidyl $$CH_2\text{—}CHCH_2OC_6H_5$$
$$\diagdown O \diagup$$

is disclosed in U.S. Pat. No. 4,127,615.

DISCLOSURE OF INVENTION

Novel perfluoroglycidyl ethers are provided having the general formula:

$$CF_2\text{—}CFCF_2OR_F \qquad\qquad\qquad I$$
$$\diagdown O \diagup$$

wherein $R_F$ is:

$$-CFR^1CFQ \qquad\qquad\qquad (i)$$
$$\ \ |\qquad\ \ |$$
$$\ \ Y\quad\ \ Y'$$

wherein $R^1$ is a carbon-carbon bond or a linear or branched perfluoroalkylene group of 1 to 12 carbon atoms;

$$Q \text{ is } -OCF_2CF=CF_2 \text{ or } -OCF_2CF\text{—}CF_2;$$
$$\qquad\qquad\qquad\qquad\qquad\qquad\qquad\ \ \diagdown O \diagup$$

Y and Y' are —F or —CF$_3$, provided that only one of Y and Y' can be —CF$_3$; or:

$$-(CF_2CFO)_nR^3Q \qquad\qquad\qquad (ii)$$
$$\qquad\ \ |$$
$$\qquad\ \ Y$$

wherein $R^3$ is a linear or branched perfluoroalkylene group of carbon content such that the moiety $$-(CF_2CFO)_nR^3$$
$$\qquad\ \ |$$
$$\qquad\ \ Y$$

does not exceed 15 carbon atoms; Y independently is —F or —CF$_3$; n is 1 to 4; and Q is as defined above. Ethers of formula I where Q is —OCF$_2$CF=CF$_2$ are useful as intermediates in the preparation of the corresponding perfluorodiglycidyl ether.

Perfluoroglycidyl ethers of formula I are prepared by contacting and reacting the corresponding perfluorodiallyl ethers with oxygen.

The ethers of formula I may be homopolymerized, or copolymerized with suitable fluorinated epoxides which include hexafluoropropene oxide, tetrafluoroethylene oxide, and other perfluorodiglycidyl ethers of formula I.

Polymers prepared from formula I glycidyl ethers provide crosslinking or cure sites and are stable elastomeric materials useful as sealants, caulks, and fabricated objects. Preferred are ethers of formula I where $R_F$ is:

$$-\underset{\underset{Y}{|}}{\overset{}{C}}FR^1\underset{\underset{Y'}{|}}{\overset{}{C}}FQ \text{ or}$$

$$-CF_2\underset{\underset{CF_3}{|}}{\overset{}{C}}FOCF_2CF_2O\underset{\underset{CF_3}{|}}{\overset{}{C}}FCF_2Q; \text{ Y and Y' are } -F;$$

and Q is $-OCF_2\underset{\diagdown\!\!\!\!\diagup\!\!\!\!\!O}{CF-CF_2}$.

Perfluorodiallyl ethers, when reacted with O$_2$, also yield, in addition to the perfluorodiglycidyl ethers of formula I, coproduct fluoroformyl difluoromethyl ethers containing one less carbon atom which have the general formula:

$$FOC-CF_2OR_F \qquad \qquad II$$

wherein R$_F$ is as defined above.

The novel perfluoroglycidyl ethers of this invention are prepared from the perfluorodiallyl ethers which are disclosed by Krespan in U.S. application Ser. No. 145,756, filed May 1, 1980 now U.S. Pat. No. 4,275,225, issued June 23, 1981. These perfluorodiallyl ethers are of the formula:

$$CF_2=CFCF_2OR_{F'}$$

wherein R$_{F'}$ is:

$$-\underset{\underset{Y}{|}}{\overset{}{C}}FR^1\underset{\underset{Y'}{|}}{\overset{}{C}}FQ^1 \qquad \qquad (i)$$

wherein R$^1$ is a carbon-carbon bond or a linear or branched perfluoroalkylene group of 1 to 12 carbon atoms; Q$^1$ is $-OCF_2CF=CF_2$; Y and Y' are $-F$ or $-CF_3$, provided that only one of the Y and Y' can be $-CF_3$; or $$-(CF_2\underset{\underset{Y}{|}}{\overset{}{C}}FO)_nR^3Q^1 \qquad (ii)$$

wherein R$^3$ is a linear or branched perfluoroalkylene group of carbon content such that the moiety $$-(CF_2\underset{\underset{Y}{|}}{\overset{}{C}}FO)_nR^3$$

does not exceed 15 carbon atoms; Y is $-F$ or $-CF_3$; n is 1 to 4; and Q$^1$ is as defined above.

The perfluoroglycidyl ethers of this invention are also prepared from perfluorodiallyl ethers of the formula:

$$CF_2=CFCF_2O(CF_2\underset{\underset{Y}{|}}{\overset{}{C}}FO)_nR^3Q^1$$

wherein R$^3$, Q$^1$, and n are as defined under (ii) above, and Y, independently, can be $-F$ or $-CF_3$.

These perfluorodiallyl ethers are prepared by
(1) mixing and reacting:
   (a) a carbonyl compound having the formula:

$$A^1-\overset{\overset{O}{\|}}{C}-Y$$

wherein A$^1$ is $$Q'CFR^1-\underset{\underset{Y'}{|}}{}$$

where R$^1$ is a carbon-carbon bond or a linear or branched perfluoroalkylene group of 1 to 12 carbon atoms; Q' is $-OCF_2CF=CF_2$; Y and Y' are $-F$ or $-CF_3$, provided that only one of Y and Y' can be $-CF_3$; or
   (b) a carbonyl compound having the formula:

$$A^2-\overset{\overset{O}{\|}}{C}-F$$

wherein A$^2$ is $$Q'R^3(OCFCF_2)_{n-1}O\underset{\underset{Y}{|}}{\overset{}{C}}F-$$
$$\phantom{Q'R^3(OCFCF_2)_{n-1}O}\underset{\underset{Y}{|}}{}$$

where R$^3$ is a linear or branched perfluoroalkylene group of carbon content such that the moiety $$R^3(OCFCF_2)_{n-1}O\underset{\underset{Y}{|}}{\overset{}{C}}F-$$
$$\phantom{R^3(OC}\underset{\underset{Y}{|}}{}$$

does not exceed 14 carbon atoms; Y independently is $-F$ or $-CF_3$; n is 1 to 4; and Q' is defined as above; with a metal fluoride of the formula MF where M is K-, Rb-, Cs-, or R$_4$N- where each $-R$, alike or different, is alkyl of 1 to 6 carbon atoms; and
(2) mixing the mixture from (1) with a perfluoroallyl compound of the formula:

$$CF_2=CF-CF_2Z$$

wherein:

Z is $-Cl$, $-Br$ or $-OSO_2F$.

The perfluoroglycidyl ethers of formula I and the fluoroformyl difluoromethyl ethers of formula II are prepared from the perfluorodiallyl ethers by partial or complete reaction with oxygen at about 20° to about 200° C., preferably about 80° to about 160° C.:

$$CF_2=CFCF_2OR'_F \xrightarrow{O_2} \qquad (2)$$

$$(x)\, CF_2\underset{\diagdown\!\!\!\!\diagup\!\!\!\!\!O}{-CFCF_2OR_F} + (y)\, FOC-CF_2OR_F + (y)\, COF_2$$
$$\phantom{(x)\, CF_2-CFCF_2OR_F}\quad I \qquad\qquad\qquad II$$

where x and y are, respectively, the mole fractions of products I and II, and R$_F$ and R$_{F'}$ are defined as above. Ethers of formula I are normally stable at the reaction temperature. Formation of ethers of formula II, together with carbonyl fluoride, is presumed to result from oxidative cleavage of an allylic double bond in the starting perfluorodiallyl ether. The by-product $COF_2$ is normally inert.

The epoxidation reaction may be carried out at pressures of about 5 to about 3000 psi, preferably about 50 to about 1500 psi. Solvents are not essential, but inert diluents such as 1,1,2-trichloro-1,2,2-trifluoroethane ($CFCl_2CF_2Cl$) or perfluorodimethylcyclobutane may be used.

Reactant proportions may vary from a large molar excess of olefin over $O_2$ (e.g., 100:1) to a large excess of $O_2$ over olefin (e.g., 100:1); a modest excess of $O_2$, e.g., about 1.1:1 to about 10:1, is normally preferred to insure complete reaction of the olefin. When preparing a perfluoroglycidyl ether of formula I wherein Q is $-OCF_2CF=CF_2$, the reaction of the starting diolefin with $O_2$ should be run with at least a 2:1 molar excess of diolefin over $O_2$, and further addition of $O_2$ should be avoided.

The epoxidation reaction is most conveniently initiated thermally, but may be catalyzed by the use of free-radical initiators or by ultraviolet irradiation in the presence of a photoactive material such as bromine. The epoxidation may be conducted in a batchwise or continuous manner.

The epoxidation product of formula I is generally isolated by direct fractional distillation, although in some cases a preliminary treatment with $Br_2$ or $Cl_2$ may be helpful. When epoxidation is carried out at lower temperatures (100°), addition of radical acceptors such as o-dichlorobenzene to the mixture just prior to fractionation is a desirable precaution against the possible presence of peroxides.

Perfluoroglycidyl ethers of formula I can be homopolymerized or copolymerized with suitable fluorinated epoxides such as HFPO, tetrafluoroethylene epoxide (TFEO), other perfluoroglycidyl ethers of formula I and perfluoroglycidyl ethers disclosed in copending U.S. Patent Application Ser. No. 250,906, filed simultaneously herewith by King et al.; HFPO and TFEO are preferred comonomers with HFPO most preferred. (Co)-polymerization proceeds in the presence of a suitable solvent and initiator at temperatures of about $-45°$ to about $+25°$ C., preferably about $-35°$ to about $0°$ C. The quantity of solvent may be from about 5 to about 40 mole percent of the total monomer feed. Suitable solvents include commercial ethers such as diethyl ether, diglyme, triglyme and tetraglyme (di-, tri-, and tetraethyleneglycol dimethyl ether), and fluorinated solvents such as 1,1,2-trichlorotrifluoroethane, chlorotrifluoroethylene, dichlorodifluoromethane, hydrogen-capped HFPO oligomers of the formula $CF_3CF_2CF_2O[CF(CF_3)CF_2O]_nCHFCF_3$, where n is 1 to 6, dimers and trimers of hexafluoropropene (HFP), and HFP itself; the latter is a preferred solvent. Solvents should be thoroughly dried, preferably by means of molecular sieves, before use.

Catalysts suitable for the (co)polymerization of formula I ethers include anionic initiators which are effective for the polymerization of hexafluoropropylene oxide (HFPO), such as carbon black or, preferably, combinations CsF-LiBr, KF-LiBr, $(C_6H_5)_3PCH_3$, -LiBr, $CsF-FOCCF(CF_3)OCF_2CF_2OCF(CF_3)COF$, $CsF-CF_3CF_2CF_2O[CF(CF_3)CF_2O]_nCF(CF_3)COF$, where n is 2 to 6; the latter catalyst wherein n is 4 to 6 is preferred. Preparation of fluoropolyethers such as that used in the last mentioned catalyst is described in U.S. Pat. No. 3,322,326. Catalyst concentration should be about 0.05 to about 1 mole percent of the total monomer feed when higher molecular weight products are desired.

The perfluoroglycidyl ethers of formula I and comonomers such as HFPO should be reasonably pure and dry before (co)polymerization. Monomers may be dried with molecular sieves or, preferably, over $KOH-CaH_2$. Dryness and high purity are necessary for the preparation of high molecular weight (co)polymers from formula I ethers.

Polymerization pressures may be in the range of from less than one atmosphere to about 20 atmospheres or more; pressures in the vicinity of one atmosphere are normally preferred.

The copolymerization of the perfluoroglycidyl ethers of formula I with HFPO, TFEO and other perfluoroglycidyl ethers can be a random copolymerization whereby the various monomers are added and reacted with one another simultaneously, or the copolymerization can be sequential, i.e., the perfluorodiglycidyl ethers of formula I wherein Q is

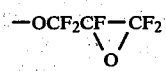

can be subsequently copolymerized with material previously polymerized, such as hexafluoropropylene oxide homopolymers as disclosed in copending U.S. Patent Application Ser. No. 250,905 filed simultaneously herewith by Darling and hexafluoropropylene oxide/perfluoroglycidyl ether copolymers as disclosed in copending U.S. Patent Application Ser. No. 250,906 filed simultaneously herewith by Krespan et al. Such a sequential copolymerization can serve as a specialized form of chain extension.

In the following examples of specific embodiments of the present invention, parts and percentages are by weight and all temperatures are in degrees C. unless otherwise specified. The most preferred polymer of the present invention is that of Example 9.

EXAMPLE 1

Perfluoro-1,2-epoxy-13,14-epoxy-4,11-dioxatetradecane and Perfluoro-12,13-epoxy-3,10-dioxatridecanoyl Fluoride

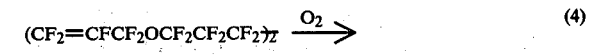

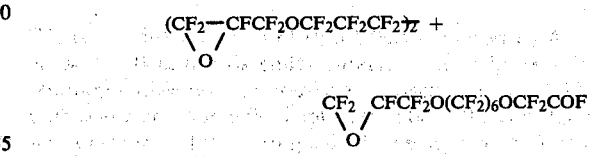

A sample of perfluoro-4,11-dioxatetradeca-1,13-diene (51.7 g, 0.087 mol, purified by distillation from conc. $H_2SO_4$) was diluted to 75 ml with dry $CFCl_2CF_2Cl$, loaded into a 100-ml stainless steel tube and heated at 140° while $O_2$ was injected in 50 psi increments. The maximum pressure was 500 psi, at which point $O_2$ consumption ceased as judged by lack of pressure drop. Distillation of the liquid products gave 39.1 g of fractions with bp 56° (95 mm)–81° (8.0 mm). Analysis by gc revealed a single major peak for all fractions with a total of 5–15% of varying impurities present. However, IR and NMR showed that this main peak represented both products. An early fraction, 6.4 g, bp 62°-64° (9 mm), was nearly pure perfluoro-12,13-epoxy-3,10-dioxatridecanoyl fluoride. IR (CFCl$_2$CF$_2$Cl): 5.28 (COF), 6.59 (epoxide), 7.5–9.5μ (CF, C—O). NMR (CCl$_4$/CFCl$_3$): $^{19}$F 13.1 (m, 1F, COF), −77.2 (t of d, J$_{FF}$ 11.6, 2.5 Hz, 2F, CF$_2$COF), −83.3 (m, 4F, CF$_2$O), −122.5 (m, 4F, CF$_2$), −125.8 (m, 4F, CF$_2$), and −156.7 ppm (t, J$_{FF}$ 18 Hz, 1F, CF) with AB groupings for ring CF$_2$ at −103,901 and −10,433 Hz (d of t, J$_{FF}$ 18.8, 9.6 Hz, 1F) and −10,617 and −10,659 Hz (d, J$_{FF}$ 17.4 Hz, 1F), and for CF$_2$ adjacent to epoxide ring at −7369, −7523, −7553, and −7706 Hz (m, 2F).

Higher-boiling cuts, 21.8 g, bp mainly 68°-70° (8 mm), contained chiefly diepoxide with epoxyacid fluoride as a major impurity. These higher cuts were combined and shaken with 200 ml of cold water for 5 min. Heat of reaction, cloudiness and some foaming were apparent. A portion of the lower layer was dried over anhydrous CaSO$_4$. It was then transferred trap-to-trap twice under vacuum to give 4.26 g of clear colorless perfluoro-1,2-epoxy-13,14-epoxy-4,11-dioxatetradecane, 99% pure by gc. IR (neat): 6.59 (epoxide) and 7.5–9.5μ (CF, C—O) with no bands for OH, C=O, or C=C detected. NMR (CCl$_4$/CFCl$_3$): $^{19}$F −83.5 (m, 4F, CF$_2$O), −122.7 (m, 4F, CF$_2$), −125.9 (m, 4F, CF$_2$), and −156.9 ppm (t, J$_{FF}$ 18 Hz, 2F, CF) with AB groupings for ring CF$_2$ at −10391 and −10658 Hz (d, J$_{FF}$ 17.4 Hz, 2F) and for CF$_2$ adjacent to epoxide ring at −7378, −7531, −7561, and −7714 Hz (m, 4F) with only trace impurities present.

Anal. Calcd for C$_{12}$F$_{22}$O$_4$: C, 23.02. Found: C, 23.68.

It is considered probable that the epoxidation reaction proceeded via the allyloxy-epoxide intermediate

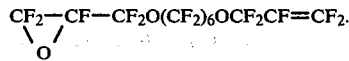

EXAMPLE 2

Perfluoro(1,2-epoxy-15,16-epoxy-6,11-dimethyl-4,7,10,13-tetraoxahexadecane)

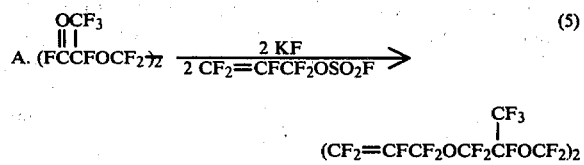

A suspension of 20.3 g (0.35 mol) of flame-dried KF in 300 ml of dry diglyme while stirred at 0°-5° while 53.0 g (0.125 mol) of perfluoro(2,7-dimethyl-3,6-dioxasuberoyl) fluoride was added. The mixture was stirred for 30 min, after which 80.5 g (0.35 mol) of perfluoroallyl fluorosulfate was added at 0°-5°. After having stirred for 3 hr at 0°-5°, then at 25° for 2 hr, the mixture was poured into 1 l of cold water. The lower layer was washed with 500 ml of water, dried over CaSO$_4$ and fractionated to afford 47.3 g (52%) of pure perfluoro(6,11-dimethyl-4,7,10,13-tetraoxahexadeca-1,15-diene). IR (neat): 5.58 (C=C), 8–9μ (CF, C—O). NMR (CCl$_4$/CFCCl$_3$): $^{19}$F −72.1 (d of t of d of d, J$_{FF}$ 24.7, ∼13.7, 13.7, 7.3 Hz, 4F, OCF$_2$C=), −80.7 (m, 6F, CF$_3$), −84.1 (m, 4F, OCF$_2$), −92.1 (d of d of t, J$_{FF}$ 52.6, 39.4, 7.3 Hz, 2F, cis-CF$_2$CF=CFF), −105.5 (d of d of t, J$_{FF}$ 118.0, 52.6, 24.7 Hz, 2F, trans-CF$_2$CF=CFF), −146.0 (t, J$_{FF}$ 21.3 Hz, 2F, CF), and −190.9 ppm (d of d of t, J$_{FF}$ 118.0, 39.4, 13.7 Hz, 2F, -CF$_2$CF=CF$_2$), with an AB pattern for OCF$_2$ at −7988, −8122, −8142, and −8258 Hz (m, 4F).

Anal. Calcd. for C$_{14}$F$_{26}$O$_4$: C, 23.15. Found: C, 23.29.

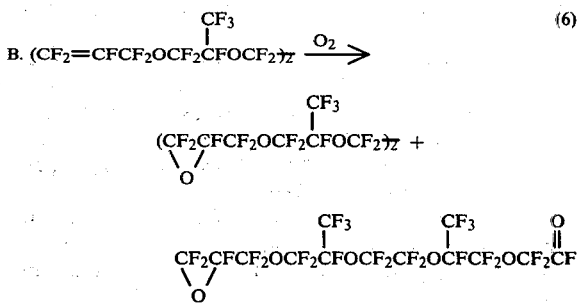

A solution of 45.7 g (0.063 mol) of the above hexadecadiene in 75 ml of CFCl$_2$CF$_2$Cl was heated at 140° in a 100-ml stainless steel-lined tube while oxygen was injected portionwise until reaction was complete. Distillation of the liquid product afforded 37.2 g of fractions with bp 63° (10 mm)–65° (4 mm) shown by IR and NMR to be perfluoro(1,2-epoxy-15,16-epoxy-6,11-dimethyl-4,7,10,13-tetraoxahexadecane containing perfluoro(14,15-epoxy-5,10-dimethyl-3,6,9,12-tetraoxapentadecanoyl) fluoride as the major impurity. Several fractions (22.7 g) was combined and contacted with CaH$_2$ while standing open to atmospheric moisture for a day. The open mixture was then stirred for 4 hr and filtered. Volatiles were transferred at 50° (0.05 mm), stirred with CaSO$_4$ for 2 hrs, and then transferred again at 45° (0.05 mm) to give 5.5 g of nearly pure diepoxide. IR (neat): 6.47 (epoxide) and 8–9μ (CF, C—O) with very weak impurity bands present at 5.28 (COF) and 6.64 (CO$_2$H).

Other fractions were shown by $^{19}$F NMR to contain about 8.2 g of diepoxide as 80% pure material, for a total of 13.7 g (29%).

EXAMPLE 3

Perfluoro(1,2-epoxy-10,11-epoxy-4,8-dioxaundecane)

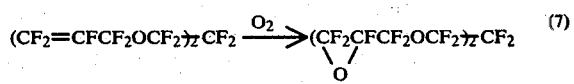

A 100-ml metal tube containing 107 g (0.24 mol) of perfluoro(4,8-dioxa-1,10-undecadiene) was heated at 140° while oxygen was injected portionwise until reaction was nearly complete. Fractionation of the liquid products gave 66.7 g, bp 42°-64° (50 mm), containing mainly diepoxide and epoxyacid fluoride. This distillate was irradiated with excess bromine to remove any olefinic material, residual bromine was evaporated, and the residue was shaken with a mixture of 250 ml of ice water and 50 ml of CFCl$_2$CF$_2$Cl. The organic layer was dried over CaSO$_4$ and distilled to give 27.5 g of nearly pure diepoxide, bp 60°-68° (100 mm). The distillate was treated with CaSO$_4$, filtered and redistilled to give 19.6 g (17%) of pure diepoxide, bp 54°-56° (50 mm). IR (CCl$_4$/CFCl$_2$CF$_2$Cl): 6.49 (epoxide), 8–9μ (CF, (C—O). NMR (CCl$_4$/CFCl$_3$): $^{19}$F −84.2 (m, 4F, OCF$_2$), −130.1 (s, 2F, CF$_2$), and −157.1 ppm (t, J$_{FF}$ 17.5 Hz, 2F, CF) with AB patterns for CF$_2$ adjacent to epoxide ring at −7399, −7550, −7594, and −7747 Hz (m, 4F) and for ring CF$_2$ at −10415 and −10,457 (d of t, J$_{FF}$ 18.7, 9.7 Hz, 2F) and −10,643 and −10,684 Hz (d, J$_{FF}$ 16.4 Hz, 2F).

Anal. Calcd. for C$_9$F$_{16}$O$_4$: C, 22.71; F, 63.85. Found: C, 22.99; F, 63.92.

EXAMPLE 4

Copolymerization of Perfluoro(1,2-epoxy-15,16-epoxy-6,11-dimethyl-4,7,10,13-tetraoxahexadecane) with Hexafluoropropylene Oxide The polymerization catalyst was prepared by reacting 2.09 g (0.0137 mol) CsF, 6.07 g (0.0273 mol) tetraglyme and 7.97 g (0.0120 mol) HFPO tetramer. The catalyst was shaken for at least 6 h and centrifuged for 30 min at 0°. To a thoroughly dried 4-neck 500-ml flask was injected 4 millimole of the prepared catalyst. The reaction mixture was then cooled to −35° C. Hexafluoropropylene (dried by passing through molecular sieves) was added at a rate of 1 g/min for a total of 20 g.

4.97 g of the diepoxide of Example 1 and 144 g of HFPO (dried by passing over KOH and CaH$_2$) were copolymerized over a period of 35.3 hr at −34° to −35°. After this period, the stirring was extremely difficult due to the almost semisolid condition of the polymer. Part of the recovered polymer, 15 g, was reacted with 10% NaOH in ethyl carbitol to a neutral point with phenolphthalein indicator. The sodium salt was decarboxylated by heating to 160° for 30 min. The isolated polymer gave ηinh of 0.195 in Freon® E3

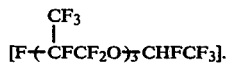

The calculated molecular weight is 200,000. Based on the 3.34% by weight of added diepoxide, the ratio of HFPO units to diglycidyl monomer units is approximately 132:1.

EXAMPLE 5

Terpolymerization of Perfluoro(1,2-epoxy-15,16-epoxy-6,11-dimethyl-4,7,10,13-tetraoxahexadecane) and Perfluoro-6,7-epoxy-4-oxaheptanenitrile with Hexafluoropropylene Oxide Two monomers were combined as follows: 2 g of the diepoxide of Example 1 were mixed with 4.67 g of the epoxynitrile. Following the procedure for HFPO copolymerization (Example 4), 6.34 g of the mixed monomers and 177 g of HFPO were copolymerized at −33° to −35° over a period of 42.3 hr. The molecular weight by inherent viscosity was 41,000. On standing at room temperature over a period of 3½ months, there was further curing of the polymer resulting in a partially solidified material. From the weight % added monomers the ratio of HFPO units to nitrile monomer units to diglycidyl monomer units is approximately 431:8:1.

EXAMPLE 6

Curing of Terpolymer of Perfluoro(1,2-epoxy-15,16-epoxy-6,11-dimethyl-4,7,10,13-tetraoxahexadecane), Perfluoro-6,7-epoxy-4-oxaheptanenitrile and Hexafluoropropylene Oxide The following was milled until a homogeneous mix was obtained: 5.46 g of the terpolymer of Example 5, 0.55 g carbon black, 0.16 g tetraphenyltin and 0.16 g magnesium oxide. The milled material was degassed by placing in a vacuum oven for 16 hr at 50°. This was then placed in a microtensile bar mold and pressed in a Carver press under 500 psi at 210° for 4 hr. At this point a soft rubbery tensile bar was obtained.

EXAMPLE 7

Copolymerization of Perfluoro(1,2-epoxy-10,11-epoxy-4,8-dioxaundecane) with Hexafluoropropylene Oxide Following the procedure for HFPO copolymerization (Example 4), 5.78 g of the diepoxide of Example 3 and 165 g of HFPO were copolymerized over a period of 51.1 h at −34° to −36°. The molecular weight by IR was 16,000. The ratio of HFPO units to diglycidyl monomer units is approximately 82:1. On standing at room temperature for 3 weeks, there was a visible increase in viscosity.

EXAMPLE 8

Copolymerization of Perfluoro-6,7-epoxy-4-oxaheptanenitrile with Hexafluoropropylene Oxide The polymerization vessel consisted of a fully glass jacketed four-neck round bottom reactor which is equipped with a paddle stirrer, Dry Ice reflux condenser, gas inlet port and a thermocouple well. The entire reactor was dried thoroughly at 200° C. in a dry nitrogen atmosphere and was assembled and kept dry with a blanket of high purity dry nitrogen. Methanol was used as a coolant and was pumped through the coolant jacket from a Neslab ULT80 low temperature circulator and refrigerator system. Initiator was prepared by adding, under dry nitrogen, 7.95 grams (7.8 milliliters, 0.0358 mole) of tetraglyme to 2.54 grams (0.0167 mole) of cesium fluoride and then adding 2.91 grams (1.75 ml, 0.0068 mole) of 2,2′-[(tetrafluoroethylene)dioxy]bis-(tetrafluoropropionyl fluoride). The mixture was shaken overnight at room temperature and then centrifuged for 30 minutes to remove unreacted cesium fluoride. With the reactor at room temperature 4 milliliters of initiator was introduced by means of syringe and the reactor was cooled to an internal temperature of between −30° to −34° C. Liquified hexafluoropropylene was used as a solvent to dilute the cold viscous initiator solution. The polymerization was carried out at −34° C. using the following monomers and diluent addition schedule. The approximate addition rates were 0.126 g/hr for perfluoro-6,7-epoxy-4-oxaheptanenitrile and 5.7 g/hr for hexafluoropropylene oxide which was purified in a two-stage (potassium hydroxide/calcium hydride) scrubber and was added as a gas in semi-batch fashion.

| Addition Time (hrs) | HFP Diluent (g) | Curesite Monomer (g) | HFPO (g) |
|---|---|---|---|
| 0.23 | 7 | 0 | 0 |
| 2.67 | | 0 | 15.2 |
| 10.3 | | 1.29 | 58.7 |
| 2.0 | 30 | | |
| 23.0 | | 2.90 | 131.0 |
| 2.0 | 30 | | |
| 22.25 | | 2.80 | 126.8 |
| Total | 67 | 6.99 | 331.7 |

EXAMPLE 9

Subsequent Copolymerization with Perfluoro-1,2-epoxy-13,14-epoxy-4,11-dioxatetradecane 30 grams of hexafluoropropylene (HFP) were added to the product of Example 8 to reduce viscosity and improve mixing of the polymer mass. Then a solution of 1.9 g of diepoxide (perfluoro-1,2-epoxy-13,14-epoxy-4,11-dioxatetradecane) in 30 grams of liquid HFP at −40° C. was added to the reactor over a period of 2 hours. The reactor was maintained at −34° C. for 24 hours. The polymer was isolated by removing the HFP diluent under vacuum at −34° C. and allowing the polymer to warm slowly to room temperature. The polymer mass was protected by a dry nitrogen atmosphere. The inherent viscosity of the polymer in Freon® E-3 at 30° C. was 0.16 dl/g corresponding to a number average molecular weight of 75,000. Freon® E-3 is 2H-heptadecafluoro-5,8-bis(trifluoromethyl)-3,6,9-trioxadodecane.

EXAMPLE 10

Heat Treatment and Vulcanization of Poly-Hexafluoropropylene Oxide Containing Nitrile Cure Site The polymer prepared as in Example 9 was heat treated at 140° C./6.7 Pa for one hour, giving a partially gelled polymer. The polymer was washed with water on a wash mill for 20 minutes at room temperature and was then dried under nitrogen at 75° C./2.67 kPa for 2 days. Then 41 g of the polymer was milled at room temperature on a roll mill with 1.24 g (3 parts per hundred rubber) of micronized tetraphenyl tin and 6.2 g (15 phr) of SAF carbon black predried under nitrogen 120° C./2.67 kPa. The compound was dried at 92° C./2.67 kPa for 3.5 hours, and 5.5 g portions were compression molded in a 63×18×1.5 mm steel mold at 210° C. and 17 MPa for 2 hours. The cured slabs were removed from the mold at room temperature and were then post cured under nitrogen according to the following schedule:

| 70° → 204° | 6 hrs |
|---|---|
| @204° | 18 hrs |
| 204° → 288° | 6 hrs |
| @288° | 18 hrs |
| @315° | 48 hrs |

Stress-strain properties of a typical vulcanizate at room temperature at:

| 100% modulus, MPa | 1.0 |
|---|---|
| Tensile-at-break, MPa | 4.6 |
| Elongation-at-break, % | 250 |
| Permanent Set, % | 4 |
| Hardness, Shore A | 30 |

O-rings prepared by compression molding and post-curing the compound under the above conditions but without the final post-curing at 315° had compression set (ASTM D395-78, Method B) at room temperature/70 hours approximately zero percent and at 204°/70 hours approximately 40 percent.

We claim:

1. A homopolymer of a perfluoroglycidylether of the formula

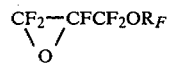

wherein $R_F$ is:

    (i)

wherein $R^1$ is a carbon-carbon bond or a linear or branched perfluoroalkylene group of 1 to 12 carbon atoms;

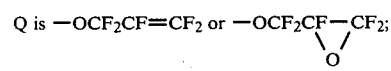

Y and Y' are —F or —CF$_3$, provided that only one of Y and Y' can be —CF$_3$; or

    (ii)

wherein $R^3$ is a linear or branched perfluoroalkylene group of carbon content such that the moiety

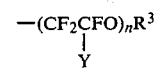

does not exceed 15 carbon atoms; Y, independently, is —F or —CF$_3$; n is 1 to 4; and Q is as defined above.

2. A copolymer of a perfluoroglycidyl ether of the formula

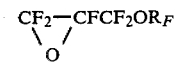

wherein $R_F$ is:

    (i)

wherein $R^1$ is a carbon-carbon bond or a linear or branched perfluoroalkylene group of 1 to 12 carbon atoms;

Q is $-OCF_2CF=CF_2$ or 

Y and Y' are —F or —CF$_3$, provided that only one of Y and Y' can be —CF$_3$; or

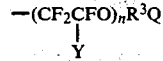 (ii)

wherein R$^3$ is a linear or branched perfluoroalkylene group of carbon content such that the moiety

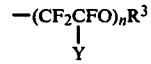

does not exceed 15 carbon atoms; Y, independently, is —F or —CF$_3$; n is 1 to 4; and Q is as defined above and at least one comonomer selected from the group consisting of hexafluoropropylene oxide, tetrafluoroethylene oxide, a different perfluoroglycidyl ether from the class of perfluoroglycidyl ethers described above and a perfluoroglycidyl ether of the formula

wherein R$^1$ is:

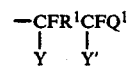 (i)

wherein R$^1$ is a carbon-carbon bond or a linear or branched perfluoroalkylene group of 1 to 12 carbon atoms; Q$^1$ is —SO$_2$F, —COF, —F, —Cl, —Br, —I, —CN, —CO$_2$H, —OC$_6$F$_5$, or —CO$_2$R$^4$ where R$^4$ is —CH$_3$ or —C$_2$H$_5$; Y and Y' are —F or —CF$_3$, provided that only one of Y and Y' can be —CF$_3$; or (ii) —CF(R$^2$)$_2$ wherein R$^2$ is —F, —CF$_2$Cl, —CF$_2$CN, —CF$_2$COF, —CF$_2$CO$_2$H, —CF$_2$OCF(CF$_3$)$_2$ or —CF$_2$CO$_2$R$^4$ where R$^4$ is defined as above; or

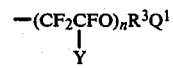 (iii)

wherein R$^3$ is a linear or branched perfluoroalkylene group of carbon content such that the moiety

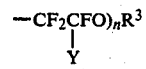

does not exceed 15 carbon atoms; Y independently is —F or —CF$_3$; n is 1 to 4; and Q$^1$ is as defined above; or (iv) —C$_6$F$_5$.

3. A copolymer of claim 2 in which the comonomer is hexafluoropropylene oxide.

4. A copolymer of a perfluorodiglycidyl ether of claim 1 and a polymer selected from the group consisting of homopolymers of hexafluoropropylene oxide, homopolymers of tetrafluoroethylene oxide, and copolymers of at least two of hexafluoropropylene oxide, tetrafluoroethylene oxide and perfluoroglycidyl ethers of the formula:

wherein R$_F^1$ is:

 (i)

wherein R$^1$ is a carbon-carbon bond or a linear or branched perfluoroalkylene group of 1 to 12 carbon atoms; Q$^1$ is —SO$_2$F, —COF, —F, —Cl, —Br, —I, —CN, —CO$_2$H, —OC$_6$F$_5$, or —CO$_2$R$^4$ where R$^4$ is —CH$_3$ or —C$_2$H$_5$; Y and Y' are —F or —CF$_3$, provided that only one of Y and Y' can be —CF$_3$; or (ii) —CF(R$^2$)$_2$
wherein R$^2$ is —F, —CF$_2$Cl, —CF$_2$CN, —CF$_2$COF, —CF$_2$CO$_2$H, —CF$_2$OCF(CF$_3$)$_2$ or —CF$_2$CO$_2$R$^4$ where R$^4$ is defined as above; or

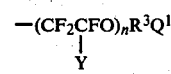 (iii)

wherein R$^3$ is a linear or branched perfluoroalkylene group of carbon content such that the moiety

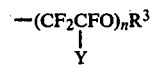

does not exceed 15 carbon atoms; Y independently is —F or —CF$_3$; n is 1 to 4; and Q$^1$ is as defined above; or (iv) —C$_6$F$_5$.

5. A copolymer of a perfluorodiglycidyl ether of claim 1 and a polymer selected from the group consisting of homopolymers of hexafluoropropylene oxide and copolymers of hexafluoropropylene oxide and perfluoroglycidyl ethers of the formula:

wherein R$_F^1$ is:

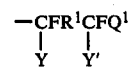 (i)

wherein R$^1$ is a carbon-carbon bond or a linear or branched perfluoroalkylene group of 1 to 12 carbon atoms; Q$^1$ is —SO$_2$F, —COF, —F, —Cl, —Br, —I, —CN, —CO$_2$H, —OC$_6$F$_5$, or —CO$_2$R$^4$ where R$^4$ is —CH$_3$ or —C$_2$H$_5$; Y and Y' are —F or —CF$_3$, provided that only one of Y and Y' can be —CF$_3$; or (ii) —CF(R$^2$)$_2$ wherein $R^2$ is —F, —$CF_2Cl$, —$CF_2CN$, —$CF_2COF$, —$CF_2CO_2H$, —$CF_2OCF(CF_3)_2$ or —$CF_2CO_2R^4$ where $R^4$ is defined as above; or

wherein $R^3$ is a linear or branched perfluoroalkylene group of carbon content such that the moiety

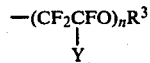

does not exceed 15 carbon atoms; Y independently is —F or —$CF_3$; n is 1 to 4; and $Q^1$ is as defined above; or (iv) —$C_6F_5$.

6. A copolymer of a perfluorodiglycidyl ether of claim 1 and a copolymer of hexafluoropropylene oxide and perfluoro-6,7-epoxy-4-oxaheptanenitrile.

7. The copolymer of claim 6 in which the perfluorodiglycidyl ether of claim 1 is perfluoro-1,2-epoxy-13,14-epoxy-4,11-dioxatetradecane.

8. The copolymer of claim 6 wherein the perfluorodiglycidyl ether of claim 1 is perfluoro-1,2-epoxy-15,16-epoxy-6,11-dimethyl-4,7,10,13-tetraoxahexadecane.

9. A vulcanized article made from a copolymer of claim 4.

* * * * *